United States Patent [19]

Monnais et al.

[11] Patent Number: 4,637,821

[45] Date of Patent: Jan. 20, 1987

[54] TINCTORIAL COMPOSITION FOR KERATIN FIBRES, BASED ON NITRATED BENZENE DYESTUFFS

[75] Inventors: Christian Monnais, Neuilly-sur-Seine; Jean Cotteret, Franconville, both of France

[73] Assignee: L'Oreal, Paris, France

[21] Appl. No.: 428,523

[22] Filed: Sep. 30, 1982

[30] Foreign Application Priority Data

Oct. 8, 1981 [LU] Luxembourg ............................ 83686

[51] Int. Cl.$^4$ .............................................. A61K 7/13
[52] U.S. Cl. .......................................... 8/415; 8/407; 8/408; 8/414; 8/428
[58] Field of Search ................... 8/414, 415, 428, 407, 8/408

[56] References Cited

U.S. PATENT DOCUMENTS

| | | | |
|---|---|---|---|
| 1,416,646 | 5/1982 | Kaltwasser et al. | 8/414 |
| 1,466,747 | 9/1923 | Onnertz | 8/414 |
| 3,049,393 | 8/1962 | Seemuller | 8/415 |
| 3,617,163 | 11/1971 | Kalopissis et al. | 8/426 |
| 3,629,330 | 12/1971 | Brody | 8/414 |
| 3,632,292 | 1/1972 | Kalopissis et al. | 8/415 |
| 3,794,676 | 2/1974 | Halasz | 8/415 |
| 3,861,868 | 1/1975 | Milbrada | 8/414 |
| 3,951,589 | 4/1976 | Alperin et al. | 8/415 |
| 4,125,601 | 11/1978 | Bugaut et al. | 8/414 |
| 4,330,291 | 5/1982 | Bugaut et al. | 8/407 |
| 4,417,896 | 11/1983 | Bugaut et al. | 8/407 |

FOREIGN PATENT DOCUMENTS

| | | | |
|---|---|---|---|
| 254395 | 5/1967 | Austria . | |
| 279053 | 2/1970 | Austria . | |
| 472216 | 6/1969 | Switzerland . | |
| 524370 | 8/1972 | Switzerland . | |
| 741334 | 11/1955 | United Kingdom | 8/414 |
| 1163385 | 9/1969 | United Kingdom | 8/414 |
| 1164824 | 9/1969 | United Kingdom . | |
| 1520787 | 8/1978 | United Kingdom . | |
| 1531605 | 11/1978 | United Kingdom . | |
| 1544127 | 4/1979 | United Kingdom . | |
| 1549752 | 8/1979 | United Kingdom . | |
| 2081735 | 2/1982 | United Kingdom . | |
| 2082207 | 3/1982 | United Kingdom . | |

OTHER PUBLICATIONS

D. Nickerson, "Color Tolerance Specification", Sep. 1944, pp. 550–570.

Primary Examiner—Albert T. Meyers
Assistant Examiner—John M. Kilcoyne
Attorney, Agent, or Firm—Fleit, Jacobson, Cohn & Price

[57] ABSTRACT

A process for dyeing keratin fibres is disclosed which involved applying:
(a) at least one dyestuff of the formula:

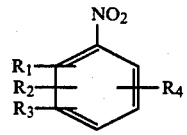

(I)

in which $R_1$ and $R_2$ independently designate hydrogen, amino, alkylamino, —NH—aliphatic—$(X)_m$, dialkylamino or —N—(aliphatic-$(X)_m)_2$, $R_3$ designates hydrogen, OH, alkoxy or —O—aliphatic-$(X)_m$ "aliphatic" designates an aliphatic radical having 2 to 4 free valencies, m designates an integer from 1 to 3 such that if m=1 X represents OH, Cl, OCH$_3$ or OCH$_2$CH$_2$OH, or, if m designates 2 or 3, X designates OH, and $R_4$ designates hydrogen, alkyl or halogen, with the proviso that at least one of $R_1$, $R_2$ and $R_3$ is other than hydrogen, and that, if $R_1$ and $R_2$ are both other than hydrogen, $R_3$ designates hydrogen,
(b) at least one dyestuff of the formula:

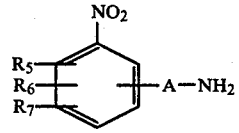

(II)

in which $R_5$ designates hydrogen, amino, aminoalkyl, NH-aliphatic-$(X)_m$, N-(alkyl)$_2$, N-(aliphatic$(X)_m)_2$, or NHCH$_2$CH$_2$NH$_2$, $R_6$ designates hydrogen, OH, alkoxy, O-aliphatic$(X)_m$ or O(CH$_2$)$_n$NH$_2$, $R_7$ designates hydrogen, alkyl or halogen, A designates-Y-(CH$_2$)—$_n$, —OCH$_2$CHOH—CH$_2$— or

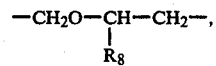

where $R_8$ designates hydrogen or methyl, Y designates oxygen or —NH— and n is an integer from 2 to 4, and m "aliphatic" and X are as defined above, with the proviso that, if Y designates —NH— and $R_6$ is other than hydrogen, $R_5$ designates hydrogen, and, if Y is an oxygen atom, $R_6$ designates hydrogen, the shade and chromaticity of the color obtained with the dyestuff(s) of formula (I) and the shade and chromaticity of the color obtained with the dyestuff(s) of formula (II) being such that $\Delta H + \Delta C$ is less than or equal to 4.5

13 Claims, No Drawings

TINCTORIAL COMPOSITION FOR KERATIN FIBRES, BASED ON NITRATED BENZENE DYESTUFFS

The present invention relates to new tinctorial compositions based on nitrated benzene dyestuffs, which are intended for use in the dyeing of keratin fibres, in particular of human hair, and to processes for dyeing these fibres by means of these compositions.

It is well known in the field of hair-dyeing to use direct dyestuffs which are nitrated benzene dyestuffs, either by themselves or together with other hair dyestuffs, such as oxidation dyestuffs or other direct dyestuffs, such as anthraquinone dyestuffs, azo dyestuffs, triarylmethane dyestuffs, indophenols, indamines and indoanilines.

Of the direct dyestuffs, nitrated dyestuffs of the benzene series provide undeniable advantages. They have a good affinity for the keratin fibres, and in particular for human hair, even when this is not sensitised, and are sufficiently compatible with conventional oxidising agents. Moreover, they generally have a low sensitivity to variations in pH in the tinctorial composition and have good compatibility with most of the ingredients used in the preparation of tinctorial compositions for hair.

Amongst the nitrated benzene dyestuffs, a distinction may be made between the nitrated benzene dyestuffs having an extranuclear amine group and the nitrated benzene dyestuffs which optionally carry an amino group directly bonded to the benzene nucleus.

In the latter class of nitrated benzene dyestuffs, which is used the most, dyestuffs which have a good resistance to light radiation, and in particular to sunlight, are readily to be found. However, these compounds often have the disadvantage that they have a low resistance to repeated washing. This is particularly the case for the well-known red dyestuff 2-nitro-1,4-diaminobenzene.

The nitrated benzene derivatives carrying an extranuclear amine group have also been recommended for dyeing hair, but have several disadvantages. These compounds give tints of which the depth and fastness to washing depends considerably on the sensitisation of the hair. In fact, after several dyeing and washing operations, a significant difference in colour is often found between the sensitised areas, in particular the ends, and the natural areas, such as the roots of the hair, with a lack of cover of the latter.

We have now found that it has been possible to obtain more uniform coloration of the hair, with improved stability to repeated washing, by combining certain nitrated derivatives of the benzene series which do not carry an extranuclear amine group with certain nitrated derivatives of the benzene series carrying an extranuclear primary amine group.

The combinations according to the invention are such that the nitrated dyestuff which is able to carry one or more amine groups directly bonded to the nucleus, or the group comprising such dyestuffs, must produce a shade substantially identical to that produced by the nitrated benzene dyestuff having an extranuclear primary amine group or the group of dyestuffs comprising these latter nitrated benzene derivatives.

This stability to washing is, surprisingly, superior to the average stability to washing obtained separately with each of the two groups of dyestuffs.

Stability to washing is to be understood to mean, in particular, preservation of the initial shade without a change in highlights, this shade remaining substantially uniform over the entire length of the hair.

The improvement in stability to washing of the dyeing can be estimated with reference to the variation in the dyeing obtained with a composition containing only one or a group of dyestuffs belonging to one of the families, used in an amount sufficient to produce, at the outset, essentially the same dyeing as that which is obtained using the combination according to the invention.

The combination according to the invention also improves the depth of colour, especially in the case of conventional nitrated dyestuffs having a low solubility.

This invention thus provides a tinctorial composition for keratin fibres, and in particular for human hair, comprising at least one dyestuff or a group of dyestuffs chosen from the nitrated benzene derivatives which may carry amino groups directly bonded to the nucleus, combined with a dyestuff or a group of dyestuffs comprising nitrated derivatives of the benzene series having an extranuclear primary amine group.

The invention also provides a process for dyeing in which such a composition is used.

The composition according to the invention is essentially characterised in that it contains:

(a) at least one nitrated benzene dyestuff, or a group of dyestuffs, corresponding to the formula:

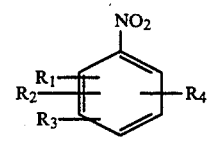
(I)

in which $R_1$ or $R_2$ independently of one another designate hydrogen, amino, alkylamino, —NH—aliphatic—$(X)_m$, dialkylamino or —N—(aliphatic—$(X)_m)_2$, $R_3$ designates hydrogen, OH, alkoxy or —O—aliphatic—$(X)_m$, m designates an integer from 1 to 3 such that if m=1, X represents OH, Cl, OCH$_3$ or OCH$_2$CH$_2$OH, or, if m designates 2 or 3, X designates OH, and $R_4$ designates hydrogen, alkyl or halogen, with the proviso that at least one of the substituents $R_1$, $R_2$ and $R_3$ is other than hydrogen, and that, if $R_1$ and $R_2$ are both other than hydrogen, $R_3$ designates hydrogen.

In these compounds, the alkyl or aliphatic radical is preferably a branched or straight-chain (saturated) radical with 1 to 4 carbon atoms, and, in the case of the aliphatic group, with m+1 free valencies, m is an integer from 1 to 3 inclusive, and, if m designates 1, X represents OH, Cl, OCH$_3$ or OCH$_2$CH$_2$OH, and, if m is greater than 1, X designates OH; in combination with:

(b) at least one nitrated dyestuff having an extranuclear primary amine group and corresponding to the formula:

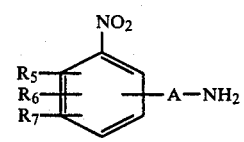
(II)

in which $R_5$ designates hydrogen, amino, aminoalkyl, NH—alkylene—$(X)_m$, N—(alkyl)$_2$, N—(aliphatic $(X)_m)_2$ or NH(CH$_2$)$_2$NH$_2$, $R_6$ designates hydrogen, OH, alkoxy, O—aliphatic $(X)_m$ or $O(CH_2)_n NH_2$ and $R_7$ designates hydrogen, alkyl or halogen. The alkyl and aliphatic radicals and m and X have the same meanings as those given above, A designates $Y—(CH_2)_n—$, $—OCH_2CHOH—CH_2—$ or

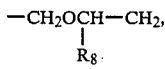

where $R_8$ designates hydrogen or methyl, n is an integer from 2 to 4 and Y can be an oxygen atom or, preferably, an NH group, with the proviso that, if Y designates the —NH group and if $R_6$ is other than hydrogen, $R_5$ designates hydrogen, and if Y designates an oxygen atom, $R_6$ designates hydrogen, it being understood that the variation in shade and chromaticity between the dyeing obtained with the dyestuff or the group of dyestuffs of the formula (I) and the dyeing obtained with the dyestuff or group of dyestuffs of the formula (II) is such that $\Delta H + \Delta C \leq 4.5$, in accordance with the Munsell evaluation.

With regard to the Munsell notation, reference may be made to the publication: Official Digest, April 1964, pages 373 to 377. In this notation, a colour is defined by the formula HV/C, in which the three parameters designate, respectively, the shade (or hue) (H), the intensity (or value) (V) and the purity or chromaticity (C), the oblique stroke being a simple convention.

It is moreover understood that the individual dyestuffs used in the case of groups of dyestuffs of the formula (I) or (II) must have, within the same group, substantially similar stability to light or washing. The same applies to their selectivity to hair.

Non-limiting examples of the dyestuffs of the formula (I) which may be mentioned are: 2,4-diaminonitrobenzene, 3,4-diaminonitrobenzene, 2,5-diaminonitrobenzene, 3-amino-4-hydroxynitrobenzene, 3-hydroxy-4-aminonitrobenzene, 2-hydroxy-5-aminonitrobenzene, 2-amino-5-hydroxynitrobenzene, 2-amino-3-hydroxynitrobenzene, 2-amino-5-N-β-hydroxyethylaminonitrobenzene, 2-amino-5-N,N-bis-β-hydroxyethylaminonitrobenzene, 2,5-N,N'-bis-β-hydroxyethylaminonitrobenzene, 2-N-β-hydroxyethylamino-5-N,N-bis-β-hydroxyethylaminonitrobenzene, 2-amino-5-N-methylaminonitrobenzene, 2-N-methylamino-5-N,N-bis-β-hydroxyethylaminonitrobenzene, 2-N-methylamino-5-[N-methyl-N-β-hyroxyethyl]-aminonitrobenzene, 2-N-β-hydroxyethylamino-5-hydroxynitrobenzene, 3-methoxy-4-N-β-hydroxyethylaminonitrobenzene, 2-N-methylamino-4-β-hydroxyethoxynitrobenzene, 2-amino-3-methylnitrobenzene, 2-N-β-hydroxyethylamino-5-aminonitrobenzene, 2-amino-4-chloro-5-N-β-hydroxyethylaminonitrobenzene, 2-amino-4-methyl-5-N-β-hydroxyethylaminonitrobenzene, 2-amino-4-methyl-5-N-methylaminonitrobenzene, 2-N-β-hydroxyethylamino-5-methoxynitrobenzene, 2-amino-5-β-hydroxyethoxynitrobenzene, 2-N-β-hydroxyethylaminonitrobenzene, 3-amino-4-N-β-hydroxyethylaminonitrobenzene, 3-β-hydroxyethoxy-4-N-β-hydroxyethylaminonitrobenzene, 2-N-methylamino-4-β,γ-dihydroxypropoxynitrobenzene, 2-N-β-hydroxyethylamino-5-β-hydroxyethoxynitrobenzene, 2-N-β-hydroxyethylamino-5-β,γ-dihydroxypropoxynitrobenzene, 3-hydroxy-4-N-β-hydroxyethylaminonitrobenzene, 2-N-methylamino-4-methyl-5-aminonitrobenzene, 2-amino-4-isopropyl-5-N-methylaminonitrobenzene, 2-N-methylamino-5-(N-methyl-N-β,γ-dihydroxypropyl)-aminonitrobenzene, 3-N-β-hydroxyethylamino-4-N-β-hydroxyethylaminonitrobenzene, 2-amino-4-methyl-5-N-β,γ-dihydroxypropylaminonitrobenzene, 2-amino-4-methyl-5-hydroxynitrobenzene and 2-N-β-hydroxyethylamino-4-N-β-hydroxyethylaminonitrobenzene.

Non-limiting examples of the dyestuffs of the formula (II) which may be mentioned are: 2-amino-5-N-β-aminoethylaminonitrobenzene, 2-N-β-aminoethylamino-5-methoxynitrobenzene, 2-N-methylamino-5-N-β-aminoethylaminonitrobenzene, 2-N-β-aminoethylamino-4-dimethylaminonitrobenzene, 3-amino-4-β-aminoethylaminonitrobenzene, 2-amino-4-methyl-5-N-β-aminoethylaminonitrobenzene, 2-N-β-aminoethylamino-5-N,N-bis-(β-hydroxyethyl)-aminonitrobenzene, 3-β-aminoethoxy-4-aminonitrobenzene, 2-N-methylamino-5-N-β-amino-n-butylaminonitrobenzene, 2-N-γ-amino-n-propylamino-5-dimethylaminonitrobenzene, 3-methoxy-4-N-β-aminoethylaminonitrobenzene, 2-N-β-aminoethylamino-5-aminonitrobenzene, 2-amino-4-chloro-5-N-β-aminoethylaminonitrobenzene, 2-N-β-aminoethylamino-4-methoxynitrobenzene, 2-N-β-aminoethylaminonitrobenzene, 2-N-β-hydroxyethylamino-5-N-β-aminoethylaminonitrobenzene, 2-N-β-aminoethylamino-4-β-hydroxyethoxynitrobenzene, 3-β-hydroxyethoxy-4-N-β-aminoethylaminonitrobenzene, 2-amino-5-aminoethoxynitrobenzene, 3-hydroxy-4-N-β-aminoethylaminonitrobenzene, 2-N-β-aminoethylamino-5-β-hydroxyethoxynitrobenzene, 2-N-β-aminoethylamino-4-hydroxynitrobenzene, 1-[(3-nitro-4-amino)-phenoxy]-3-amino-propan-2-ol, 1-[(3-methylamino-4-nitro)-phenoxy]-3-amino-propan-2-ol, 2-[2-hydroxy-3-N-β-hydroxyethylamino-6-nitro]-benzyloxy-ethylamine and 2-[2-hydroxy-3-N-β-hydroxypropylamino-6-nitro]-benzyloxy-propylamine.

These dyestuffs can also be used in the form of their salts, and in particular the dyestuffs of the formula (II) can be used either in the free form or in the form of salts, such as hydrochloride, hydrobromide and sulphate.

The nitrated dyestuffs having an extranuclear primary amine group, of the formula (II), are preferably present in amounts of 1 to 90% by weight, based on the total amount of nitrated dyestuffs employed, and preferably in amounts of 5 to 70%.

The total amount of nitrated benzene dyestuffs used in the compositions according to the invention is generally 0.005 to 3% by weight, preferably 0.01 to 2% by weight, based on the weight of the composition.

The compositions of the present invention can be used for direct dyeing of hair or for oxidation dyeing.

If the compositions are used for direct dyeing, they need contain only the combination of nitrated benzene dyestuffs defined above.

According to one embodiment of the invention, these compositions also contain other known direct dyestuffs, such as anthraquinone dyestuffs, azo dyestuffs, triarylmethane dyestuffs, benzoquinone dyestuffs or azine dyestuffs.

The direct dyestuffs other than the various nitrated benzene dyestuffs necessarily used according to the invention are typically present in the compositions in amounts of from 0.01% to 5% by weight, preferably from 0.05 to 2% by weight, based on the weight of the composition.

In the present invention, direct dyestuffs having a relatively weak fastness to repeated washing can be used with the nitrated benzene dyestuffs of the formula (I), and direct dyestuffs having a good fastness to shampooing, and more particularly basic dyestuffs, such as aminoanthraquinones and dyestuffs belonging to the Basic class of the Colour Index, can be used with the nitrated dyestuffs having an extranuclear primary amine group, of the formula (II). In the case where those direct dyestuffs other than the nitrated derivatives of the benzene series are used, it will of course be desirable for the first group of dyestuffs comprising the nitrated benzene dyestuffs of the formula (I) and the other direct dyestuffs having a low stability to washing to produce a shade and purity substantially similar to that obtained with the group comprising nitrated dyestuffs having an extranuclear primary amine group, of the formula (II), and the other direct dyestuffs having a good stability to washing. In this case also, the relationship $\Delta H + \Delta C \leq 4.5$ must be fulfilled.

In the case where the compositions according to the invention are used in the form of an oxidation tinctorial composition, they may contain so-called oxidation dyestuffs, that is to say compounds which are not dyestuffs in themselves but which are converted into dyestuffs by condensation in an oxidising medium. In this case, the oxidation dyestuffs impart a basic dyeing to the keratin fibres treated, the combination of direct dyestuffs according to the invention essentially serving to shade this basic dyeing.

Of the oxidation dyestuffs, a distinction is made between, on the one hand, oxidation dyestuff precursors of the para-type, chosen from diaminobenzenes, diaminopyridines and aminophenols, of which the functional groups are in the para-position relative to one another, and oxidation dyestuff precursors of the ortho type, of which the functional groups are in the ortho-position relative to one another, and, on the other hand, compounds called modifiers or couplers, chosen from meta-diaminobenzenes, meta-diaminopyridines, meta-aminophenols, meta-diphenols and also phenols, pyrazolones, mono- or di-hydroxylated derivatives of naphthalene and diketone derivatives. The oxidation dyestuff precursors of the ortho- or para-type can be present in the form of free compounds or salts, typically in amounts from 0.005 to 10% by weight, based on the total weight of the composition.

These couplers can be used in the tinctorial compositions of the invention in the form of free compounds or in the form of salts, typically in amounts from 0.005 to 10% by weight, preferably from 0.01 to 5% by weight, based on the total weight of the composition.

These compositions can also contain agents which enable the pH to be adjusted to a value of, say, 1 to 11.5, preferably 4 to 10.5. For better development of the nitrated dyestuffs having an extranuclear primary amine group, it may be advantageous to use tinctorial compositions having a pH greater than 8. The pH of these compositions can be adjusted to the desired value with the aid of an alkalising agent, such as ammonia, sodium carbonate, potassium carbonate, or ammonium carbonate, sodium hydroxide or potassium hydroxide, alkanolamines, such as mono-, di- or tri-ethanolamine, 2-methyl-2-aminopropanol or 2-methyl-2-aminopropane-1,3-diol, and alkylamines, such as ethylamine or triethylamine. These compositions may also contain antioxidising agents, and/or reducing agents, in particular reducing agents having a high electronegative oxidation potential at an alkaline pH, in particular organic sulphur acids, such as thiolactic acid, thioglycolic acid and cysteine, ascorbic acid and derivatives thereof and alkali metal bisulphites. These reducing agents are suitably present in amounts of 0.05 to 1.5% by weight, preferably 0.1 to 1% by weight, based on the total weight of the composition.

The tinctorial compositions according to the invention may be in diverse forms, in particular in the form of solutions, gels, creams, oils or any other appropriate form for dyeing hair, and may be formulated as an aerosol in the presence of a propellant.

Numerous cosmetically acceptable ingredients can be used for this purpose. These compositions may contain, in particular, anionic, cationic, non-ionic or amphoteric surface-active agents or mixtures thereof. Surface-active agents which may be mentioned are alkylbenzenesulphonates and alkylnaphthalenesulphonates, sulphates, ether-sulphates and sulphonates of fatty alcohols, quaternary ammonium salts, diethanolamides of fatty acids, polyoxyethyleneated and polyglycerolated acids and alcohols, polyoxyethyleneated and polyglycerolated alkylphenols, and polyoxyethyleneated alkyl-sulphates. Cationic and/or non-ionic surface-active agents are preferably used. The surface-active compounds are suitably present in the compositions according to the invention in amounts of 0.5 to 55% by weight, preferably 4 to 40% by weight, based on the total weight of the composition.

These compositions may also contain organic solvents to dissolve compounds which are not sufficiently soluble in water. Examples of solvents which may be mentioned are lower alkanols, such as ethanol or isopropanol, glycerol, glycols or glycol ethers, such as 2-butoxyethanol, ethylene glycol, propylene glycol or diethylene glycol monoethyl or monomethyl ether, and mixtures thereof. These solvents are preferably present in amounts from 1 to 40% by weight, more particularly from 5 to 30% by weight, based on the total weight of the composition.

These compositions may also be thickened, preferably with sodium alginate, gum arabic and cellulose derivatives, such as methylcellulose, hydroxyethylcellulose, hydroxypropylethylcellulose, carboxymethylcellulose and various polymers having this group, such as derivatives of acrylic acid. It is also possible to use inorganic thickening agents, such as bentonite. These thickening agents are preferably present in amounts of 0.5 to 5% by weight, in particular 0.5 to 3% by weight, based on the total weight of the composition.

It is, of course, possible to add any other adjuvant usually employed in tinctorial compositions for hair, in particular penetration agents, sequestering agents, film-forming agents, buffers and perfumes, to the compositions according to the invention.

The compositions according to the invention, with the addition of an oxidising agent in the case of an oxidation tinctorial composition, can be applied to the hair with a fixing period from, say, 2 minutes to 1 hour 30 minutes, preferably 5 minutes to 1 hour. The dyed hair is rinsed, optionally shampooed, and dried.

According to a variant of the present invention, the process for dyeing hair is carried out in two steps, a composition containing at least the dyestuff or group of dyestuffs of the formula (I) being applied in a first step and a composition containing the dyestuff or group of dyestuffs of the formula (II) being applied in a second step. These partial compositions correspond to the definitions given above and, exactly as mentioned above, may contain other dyestuffs.

One of these compositions may also contain oxidation dyestuffs and can be mixed with an oxidising agent at the time of use. Such a procedure can be used, in particular, in the case where the nitrated benzene dyestuffs of the formula (I) or the nitrated benzene dyestuffs having an extranuclear primary amine group, of the formula (II), are not stable in the medium suitable for the other composition, in particular in the case of oxidation dyeing.

In this case, one of the processes such as are described in French Patent Application No. 2,421,607, can, in particular, be applied.

The Examples which follow further illustrate this invention.

The Munsell notations indicated above, in which H defines the shade and enables a distinction to be made between blue, red, yellow and the like, V enables a distinction to be made between a light colour and a dark colour and varies from 0 (black) to 10 (white), and C enables a distinction to be made between dull colours and bright colours, grey having a value of C=0, are used to determine the shades of hair which has been dyed and, where relevant, subjected to repeated washing.

The variations in colour were determined by applying the Nickerson formula $\Delta E = 0.4 \times CO \, dH + 6 \, dV + 3 \, dC$, which is mentioned, in particular, in Colour in Business, Science and Industry, Judd WYSZECKI, Wiley Interscience.

An apparatus of the Ahiba Texomat G 6 B type used in the textile industry was used for the washing tests. The dyed hair-pieces are enclosed in a little metal basket and are subjected to a to-and-fro movement in a cylindrical glass vessel containing 40 cm$^3$ of a shampoo solution. Simultaneously with the to-and-fro movement, rotation about the axis of the glass cylinder is effected.

The shampoos which were used were as follows: type S1 shampoo: based on 0.05% of the ammonium salt of sulphated oxyethyleneated lauryl alcohol and having a final pH of 7.5; and type S2 shampoo: dilute solution containing 0.12% of oxyethyleneated copra diethylamine lactate and having a final pH of 4.5. The permed hair had been treated with a composition which comprised 8% of thioglycolic acid and 2% of thiolactic acid and having a pH of 8.2, and a fixing composition comprising 2.5% of hydrogen peroxide.

In the Examples which follow, the compositions are brought to the pH indicated by addition of citric acid or 2-amino-2-methyl-propanol.

EXAMPLE 1

The following tinctorial composition having a pH of 9.5 is prepared:
dyestuffs: x g
nonylphenol oxyethyleneated with 9 mols of ethylene oxide: 8 g
lauric diethanolamide: 2 g
2-ethoxyethanol: 10 g
distilled water, q.s.p.: 100 g.

The following compositions are used:

| Dyestuffs | Compositions | | | |
|---|---|---|---|---|
| | 1 A | 1 B | 1 C | 1 D |
| 2-Amino-5-hydroxy-nitrobenzene | 0.3 | | 0.6 | 0.3 |
| 2-N—β-Aminoethylamino-5-N—β-hydroxyethoxynitrobenzene | | 0.11 | | 0.11 |

On human hair, tinctorial compositions 1A and 1B lead to extremely close golden copper-coloured shades. $\Delta H + \Delta C$ is equal to 1.5 on 90% white hair and $\Delta H + \Delta C$ is equal to 3 on 90% white permed hair.

Composition 1D is applied to 90% white hair on the one hand, and to 90% white hair sensitised by permanent waving. The fixing time is 20 minutes, and the hair is rinsed and dried.

This procedure is followed by washing with a type S1 shampoo, and the hair-piece washed in this manner is then compared with a dyed hair-piece which has not been subjected to shampooing.

It is found that the dyeing thus obtained has a good stability to repeated washing.

If a composition containing only the dyestuff used in Example 1A is employed in proportions leading to a shade similar to that obtained for composition 1D, it is found that the dyeing, in particular on hair which has been sensitised by permanent waving, is considerably less fast to repeated washing.

EXAMPLE 2

The following tinctorial compositions having a pH of 9.5 are prepared:
dyestuffs: x g
nonylphenol oxyethyleneated with 9 mols of ethylene oxide: 8 g
lauric diethanolamide: 2 g
2-ethoxyethanol: 10 g
distilled water, q.s.p.: 100 g

| Dyestuffs | Compositions | | | |
|---|---|---|---|---|
| | 2A | 2B | 2C | 2D |
| 2-Amino-5-N—β-hydroxyethyl-aminonitrobenzene | 0.25 | — | 0.55 | 0.25 |
| 3-Hydroxy-4-N—β-hydroxyethyl-aminonitrobenzene | 0.1 | — | 0.18 | 0.1 |
| 2-Amino-4-methyl-5-hydroxynitrobenzene | 0.2 | — | 0.4 | 0.2 |
| 2-N—β-hydroxyethylamino-5-hydroxynitrobenzene | 0.05 | — | 0.1 | 0.05 |
| 2-Amino-5-N—β-aminoethyl-aminonitrobenzene monohydrobromide | — | 0.2 | — | 0.2 |
| 3-β-Aminoethoxy-4-amino-nitrobenzene | — | 0.04 | — | 0.04 |
| 2-N—β-Aminoethylamino-5-β-hydroxyethoxynitrobenzene | — | 0.1 | — | 0.1 |

Tinctorial compositions 2A and 2B lead to very close red copper-coloured shades on 90% white human hair or on 90% white permed human hair. $\Delta H + \Delta C = 1$ on 90% white hair. $\Delta H + \Delta C = 0.5$ on 90% white permed hair.

Tinctorial composition 2D comprising the combination according to the invention is applied to hair with a fixing time of 20 minutes followed by rinsing and drying. The dyeing obtained is an intense red copper-coloured shade.

Composition 2C is a composition containing only the dyestuffs of the formula (I) in amounts leading essentially to the same shade as that obtained with the tinctorial composition 2D according to the invention but using only nitrated benzene dyestuffs and not including the nitrated benzene dyestuffs having an extranuclear primary amine group.

If the procedure in Example 1 is repeated, with several successive shampooings with the type S1 shampoo, it is found that the shade obtained with composition 2D is substantially more fast to repeated washing than the shade obtained with tinctorial composition 2C.

EXAMPLE 3

The following tinctorial compositions having a pH of 9.5 are prepared:
  dyestuffs: x g
  nonylphenol oxyethyleneated with 9 mols of ethylene oxide: 8 g
  lauric diethanolamide: 2 g
  2-ethoxyethanol: 10 g
  2-ethoxyethanol: 10 g
  distilled water, q.s.p.: 100 g The dyestuffs used in the compositions are given in the table which follows:

| Dyestuffs | Compositions | | | | | |
| --- | --- | --- | --- | --- | --- | --- |
| | 3A | 3B | 3C | 3D | 3E | 3F |
| 2,5-Diaminonitrobenzene | 0.15 | | | 0.45 | 0.15 | 0.15 |
| 2-Amino-4-methyl-5-N—$\beta$-aminoethylaminonitrobenzene | | 0.075 | | | | 0.075 |
| 2-Amino-4-chloro-5-N—$\beta$-aminoethylaminonitrobenzene monohydrochloride | | | 0.13 | | 0.13 | |

It is found that, on 90% white human hair, tinctorial compositions 3A, 3B and 3C lead to red shades which are extremely close in respect of highlights.

On 90% white hair $\Delta H + \Delta C = 2.8$ (for 3A and 3B)

$\Delta H + \Delta C = 1.5$ (for 3A and 3C)

On 90% white permed hair $\Delta H + \Delta C = 4$ (for 3A and 3B)

$\Delta H + \Delta C = 3.5$ (for 3A and 3C)

Tinctorial compositions 3E and 3F are compositions according to the invention comprising a nitrated benzene dyestuff which does not carry an extranuclear primary amine group and a nitrated dyestuff having an extranuclear primary amine group. These compositions lead to an intense red shade after fixing for 20 minutes, rinsing and drying.

Composition 3D gives virtually the same shade as that obtained with compositions 3E and 3F, but using only the nitrated dyestuff of the formula (I) used in Example 3A.

When type S1 shampoos are repeatedly applied as in Examples 1 and 2, it is found that the dyeing obtained with the composition of Example 3E or 3F has a clearly better stability on sensitised or non-sensitised hair in comparison with that obtained with composition 3D containing only the dyestuff of the formula (I).

EXAMPLE 4

The following tinctorial compositions having a pH of 9.5 are prepared:
  dyestuffs: x g
  nonylphenol oxyethyleneated with 9 mols of ethylene oxide: 8 g
  lauric-diethanolamide: 2 g
  2-ethoxyethanol: 10 g
  distilled water, q.s.p.: 100 g
The dyestuffs are used in the following amounts:

| Dyestuffs | Compositions | | | |
| --- | --- | --- | --- | --- |
| | 4A | 4B | 4C | 4D |
| 2-N—Methylamino-5-N,N—bis-$\beta$-hydroxyethylaminonitrobenzene | 0.3 | — | 0.75 | 0.3 |
| 2-N—Methylamino-4-$\beta$,$\gamma$-dihydroxypropoxynitrobenzene | 0.3 | — | 0.6 | 0.3 |
| 3-N—$\beta$-Hydroxyethylamino-4-N—$\beta$-hydroxyethylaminonitrobenzene | 0.1 | — | 0.25 | 0.1 |
| 2-N—$\beta$-Hydroxyethylamino-5-$\beta$-hydroxyethoxynitrobenzene | 0.05 | — | 0.12 | 0.05 |
| 2-N—$\beta$-Aminoethylamino-5-N,N—bis-$\beta$-hydroxyethylaminonitrobenzene dihydrochloride | — | 0.2 | — | 0.2 |
| 2-N—$\beta$-Aminoethylamino-4-methoxynitrobenzene monohydrochloride | — | 0.15 | — | 0.15 |
| 3-Amino-4-N—$\beta$-aminoethylaminonitrobenzene dihydrochloride | — | 0.05 | — | 0.05 |

Applied to human hair, tinctorial compositions 4A and 4B lead to extremely close natural golden shades.

$\Delta H + \Delta C = 1.5$ on 90% white hair.

$\Delta H + \Delta C = 0.5$ on 90% white permed hair.

Tinctorial composition 4D according to the invention leads to a strong natural golden shade after application to hair, with fixing for 20 minutes, rinsing and drying.

Tinctorial composition 4C gives virtually the same shade as that obtained with tinctorial composition 4D using only the dyestuffs of Example 4A.

When the hair is washed repeatedly with the aid of an S1 shampoo, it is found that an improved stability of the dyeing is obtained with the aid of tinctorial composition 4D.

EXAMPLE 5

The following composition is prepared:
  direct nitrated dyestuffs: x g
  1,4-diaminobenzene: 0.15 g
  1-amino-4-hydroxybenzene: 0.05 g
  1,3-dihydroxybenzene: 0.1 g
  6-hydroxyethoxy-1,3-diaminobenzene dihydrochloride: 0.03 g
  1-phenyl-3-methyl-5-pyrazolone: 0.15 g
  1,4-dihydroxybenzene: 0.15 g
  sodium bisulphite of 35° Bé strength: 1.3 g
  oleyl alcohol glycerolated with 2 mols of glycerol: 5 g
  oleic alcohol glycerolated with 4 mols of glycerol: 5 g
  oleic acid: 5 g
  oleic diethanolamide: 12 g
  oleyl-diethanolamine: 5 g
  ethyl alcohol: 10 g
  2-ethoxyethanol: 12 g
  ethylenediaminetetraacetic acid: 0.2 g
  ammonia of 22° Bé strength: 10.2 g
  distilled water, q.s.p.: 100 g The tinctorial compositions are prepared using the direct nitrated dyestuffs indicated in the table which follows:

| Dyestuffs | Compositions | | | |
| --- | --- | --- | --- | --- |
| | 5A | 5B | 5C | 5D |
| 2-Amino-4-methyl-5-N—$\beta$-hydroxyethylaminonitrobenzene | 0.15 | | 0.30 | 0.15 |
| 2-N—$\beta$-Hydroxyethylamino- | 0.07 | | 0.13 | 0.07 |

| Dyestuffs | \multicolumn{4}{c}{Compositions} |
|---|---|---|---|---|
| | 5A | 5B | 5C | 5D |
| 5-hydroxynitrobenzene 2-Amino-4-methyl-5-N—β-amino-ethylaminonitrobenzene | | 0.12 | | 0.12 |

On human hair, tinctorial compositions 5A and 5B diluted weight for weight with hydrogen peroxide of 20 volumes strength lead to shades which are extremely close in respect of the highlight, which is a light pearly red.

$\Delta H + \Delta C = 3$ for a dyeing on 90% white hair with compositions 5A and 5B containing no oxidation dyestuffs.

$\Delta H + \Delta C = 0.5$ for the same compositions applied to 90% white permed hair. On application to hair for 30 minutes followed by rinsing and drying, tinctorial composition 5D diluted weight for weight with hydrogen peroxide of 20 volumes strength leads to a pearly red blond shade.

Tinctorial composition 5C, when applied under the same, conditions gives virtually the same shade as that obtained with composition 5D using only the direct dyestuffs employed in composition 5A.

After repeated washing with the aid of the type S1 shampoo, it is found that the dyeings obtained with the composition from Example 5D are clearly more fast than the dyeing obtained with the composition from Example 5C.

If the type S2 shampoo is used instead of the type S1 shampoo, similar results are observed.

EXAMPLE 6

The following tinctorial compositions having a pH of 9.5 are prepared:
dyestuffs: x g
nonylphenol oxyethyleneated with 9 mols of ethylene oxide: 8 g
lauric diethanolamide: 2 g
2-ethoxyethanol: 10 g
distilled water, q.s.p.: 100 g
The following tinctorial compositions are prepared with the dyestuffs indicated in the table below:

| Dyestuffs | \multicolumn{4}{c}{Compositions} |
|---|---|---|---|---|
| | 6A | 6B | 6C | 6D |
| 2-N—Methylamino-4-β,γ-dihydroxy-propoxynitrobenzene | 0.25 | | 0.6 | 0.25 |
| 2-N—β-Aminoethylamino-4-methoxynitrobenzene monohydrochloride | | 0.12 | | 0.12 |

On human hair, tinctorial compositions 6A and 6B lead to extremely close dull golden shades.

$\Delta H + \Delta C = 3$ on 90% white hair $\Delta H + \Delta C = 2.5$ on 90% white permed hair Tinctorial composition 6D according to the invention leads to an intense golden dyeing after application to hair for 20 minutes, followed by rinsing and drying. Tinctorial composition 6C gives virtually the same shade as that obtained with tinctorial composition 6D using only the nitrated dyestuff employed in composition 6A.

If the hair is washed repeatedly with the aid of the type S1 shampoo, it is found that the dyeing obtained with the composition from Example 6D is clearly more fast than the dyeing obtained with the aid of composition 6C.

EXAMPLE 7

The following tinctorial compositions having a pH of 9.5 are prepared:
dyestuffs: x g
nonylphenol oxyethyleneated with 9 mols of ethylene oxide: 8 g
lauric diethanolamide: 2 g
2-ethoxyethanol: 10 g
distilled water, q.s.p.: 100 g
The following dyestuffs are used in these tinctorial compositions:

| Dyestuffs | \multicolumn{4}{c}{Compositions} |
|---|---|---|---|---|
| | 7A | 7B | 7C | 7D |
| 2-N—Methylamino-5-N—methyl-N—β-hydroxyethylaminonitrobenzene | 0.2 | | 0.5 | 0.2 |
| 2-N—β-Aminoethylamino-5-N,N—bis-β-hydroxyethylaminonitrobenzene dihydrochloride | | 0.08 | | 0.08 |

On human hair, tinctorial compositions 7A and 7B lead to extremely close shades of a pearly ash-grey.

$\Delta H + \Delta C = 1.5$ on 90% white hair $\Delta H + \Delta C = 1$ on 90% white permed hair.

After application to hair for 20 minutes, followed by rinsing and drying, composition 7D according to the invention leads to an intense pearly ash-grey dyeing. Tinctorial composition 7C gives virtually the same shade as that obtained with tinctorial composition 7D using only the nitrated dyestuff employed in composition 7A. After the hair has been washed repeatedly with the type S1 shampoo, it is found that the dyeings obtained with the aid of composition 7D are clearly more fast to repeated washing than the dyeing obtained with the composition from Example 7D.

EXAMPLE 8

The following oxidation tinctorial compositions are prepared:
direct nitrated dyestuffs: x g
2,6-dimethyl-1,4-diaminobenzene dihydrochloride: 0.17 g
1-amino-4-hydroxybenzene: 0.05 g
2-methyl-1,3-dihydroxybenzene: 0.12 g
6-methyl-1-hydroxy-3-N-β-hydroxyethylaminobenzene: 0.05 g
1-hydroxynaphthalene: 0.02 g
1-phenyl-3-methyl-5-pyrazolone: 0.15 g
1,4-dihydroxybenzene: 0.15 g
sodium bisulphite of 35° Bé strength: 1.30 g
oleyl alcohol glycerolated with 2 mols of glycerol: 5 g
oleyl alcohol glycerolated with 4 mols of glycerol: 5 g
oleic acid: 5 g
oleic diethanolamide: 12 g
oleyl-diethanolamine: 5 g
ethyl alcohol: 10 g
2-ethoxyethanol: 12 g ethylenediaminetetraacetic acid: 0.2 g
ammonia of 22° Bé strength: 10.2 g
distilled water, q.s.p.: 100 g The nitrated dyestuffs used in the composition are as follows:

| Dyestuffs | Compositions | | | |
|---|---|---|---|---|
| | 8A | 8B | 8C | 8D |
| 2-Amino-3-hydroxy-nitrobenzene | 0.2 | — | 0.4 | 0.2 |
| 2-Amino-5-hydroxy-nitrobenzene | 0.05 | — | 0.11 | 0.05 |
| 2-N—β-Aminoethylamino-5-β-hydroxyethoxy-nitrobenzene | — | 0.1 | — | 0.1 |
| 3-Amino-4-N—β-aminoethylaminonitrobenzene dihydrochloride | — | 0.08 | — | 0.08 |
| 2-N—β-Aminoethylamino-nitrobenzene monohydrochloride | — | 0.04 | — | 0.04 |

On human hair, tinctorial compositions 8A and 8B diluted weight for weight with hydrogen peroxide of 20 volumes strength lead to shades which are extremely close in respect of the highlight, which is golden. The variation of shade and chromaticity for a dyeing obtained with the aid of compositions 8A and 8B but containing no oxidation dyestuffs is:

$\Delta H + \Delta C = 1$ on 90% white hair $\Delta H + \Delta C = 3$ on 90% white permed hair.

Tinctorial composition 8D according to the invention, which contains the two groups of dyestuffs, leads, after weight for weight dilution with hydrogen peroxide of 20 volumes strength, application to hair for 30 minutes, rinsing and washing, to a dyeing with an intense golden blond shade.

Tinctorial composition 8C under the same conditions gives virtually the same shade as that obtained with tinctorial composition 8D using only the nitrated dyestuffs present in tinctorial composition 8A.

When hair which has been thus dyed is washed repeatedly with the aid of the type S1 shampoo, it is found that the dyeing obtained with the composition from Example 8D is clearly more fast than the dyeing obtained with the aid of the composition from Example 8C. The superiority of the composition from Example 8D is more marked on sensitised hair.

EXAMPLE 9

The following compositions are prepared:

| Composition X | |
|---|---|
| Dyestuffs | x g |
| 2-Ethoxyethanol | 5 g |
| Hydroxyethylcellulose (Cellosize WP O3H) | 3.3 g |
| Citric acid q.s.p. | pH 3 |
| Distilled water q.s.p. | 100 g |
| Composition Y | |
| Dyestuffs | x g |
| Hydroxyethylcellulose (Cellosize WP O3H) | 3.3 g |
| Ammonia of 22° Be strength | 9.3 g |
| Distilled water q.s.p. | 100 g |

The following dyestuffs are used:

| Dyestuffs | Compositions | | |
|---|---|---|---|
| | 9 A composition (X) | 9 B composition (Y) | 9 C composition (X) |
| 3-Amino-4-N—β-hydroxyethylamino-nitrobenzene | 0.2 | — | 0.24 |
| 2-N—β-Hydroxyethyl-amino-5-β,γ-dihydroxy-propoxynitrobenzene | 0.065 | — | 0.075 |
| 2-N—Aminoethylamino-5-methoxynitrobenzene monohydrochloride | — | 0.047 | — |
| 3-Amino-4-N—β-aminoethylaminonitrobenzene dihydrochloride | — | 0.03 | — |
| 2-N—β-Aminoethylamino-nitrobenzene monohydrochloride | — | 0.015 | — |

On human hair, tinctorial compositions 9A and 9B lead to extremely close copper-coloured golden shades.

$\Delta H + \Delta C = 2.5$ on 90% white hair $\Delta H + \Delta C = 2$ on 90% white permed hair For dyeing of hair, tinctorial composition 9A is applied in a first step, the hair is rinsed and dried, and tinctorial composition 9B is then applied. An intense copper-coloured golden shade results.

Tinctorial composition 9C gives virtually the same shade as when compositions 9A and 9B are applied successively.

The dyeing obtained by successive application of compositions 9A and 9B according to the invention, and the dyeing obtained with composition 9C are then washed repeatedly. It is found that the dyeing obtained by successive application of compositions 9A and 9B is clearly more fast than the dyeing obtained with the composition from Example 9C.

EXAMPLE 10

The following tinctorial compositions are prepared:
dyestuffs: x g
nonylphenol oxyethyleneated with 9 mols of ethylene oxide: 8 g
lauric diethanolamide: 2 g
2-ethoxyethanol: 10 g
pH agent; qsp: pH 9.5
distilled water; qsp: 100 g The dyestuffs are used in the following amounts:

| Dyestuffs | 10A | 10B | 10C | 10D |
|---|---|---|---|---|
| 2-N—β-Aminoethylamino-5-amino-nitrobenzene dihydrochloride | 0.03 | | | 0.03 |
| 2-Amino-5-β-aminoethoxy-nitrobenzene monohydrochloride | 0.15 | | | 0.15 |
| 2-Amino-5-β-hydroxyethoxy-nitrobenzene | | 0.35 | 0.75 | 0.35 |
| 2-Amino-4-methyl-5-N—β-hydroxyethylaminonitrobenzene | | 0.05 | 0.08 | 0.05 |

On human hair, tinctorial compositions 10A and 10B lead to extremely close golden copper-coloured shades.

$\Delta H + \Delta C = 1$ on 90% white hair $\Delta H + \Delta C = 1.5$ on 90% white permed hair.

After application to hair for 30 minutes, followed by rinsing and drying, composition 10D according to the invention leads to an intense golden copper-coloured dyeing.

Composition 10C gives virtually the same shade as that obtained by applying composition 10D but this time using only the nitrated dyestuffs employed in composition 10B.

The dyeing obtained with composition 10D is clearly more fast to repeated washing than the dyeing obtained with composition 10C.

The reference Examples which follow describe the preparation of certain of the compounds used in the compositions according to the invention.

REFERENCE EXAMPLE 1

Preparation of
2-methyl-4-amino-5-nitro-N-β-hydroxyethylaniline

The equation is as follows:

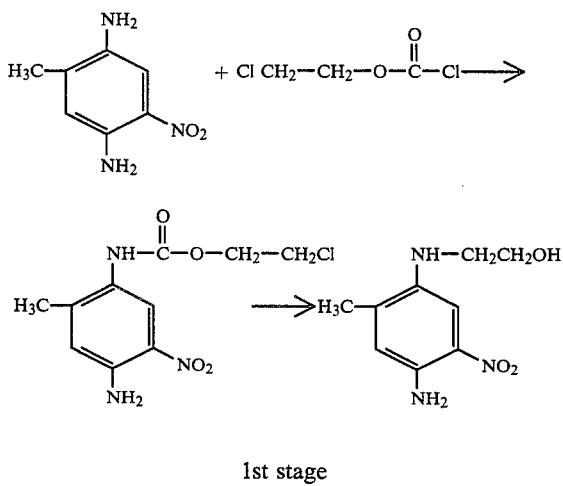

1st stage

Preparation of β-chloroethyl
N-(2-methyl-4-amino-5-nitrophenyl)-carbamate 0.6 mol (100 g) of 2-methyl-4-amino-5-nitroaniline and 0.36 mol (50 g) of potassium carbonate are introduced into 500 ml of dioxane to which 145 ml of water have been added. The mixture is brought to 90° C., while stirring, and 0.6 mol (86 g) of chloroethylchloroformate is added a little at a time, in the course of 10 minutes. When the addition has ended, heating at 90° C. is continued for 10 minutes and the reaction mixture is cooled to 15° C. and the expected product is filtered off with suction. After being washed with a little dioxane and then with water and alcohol, the product is recrystallised from dioxane and then dried in vacuo. It has a melting point of 192° C.

| Analysis | Calculated for $C_{10}H_{12}N_3O_4Cl$ | Found |
|---|---|---|
| C % | 43.87 | 43.85 |
| H % | 4.39 | 4.43 |
| N % | 15.35 | 15.25 |
| O % | 23.40 | 23.60 |
| Cl % | 12.98 | 12.78 |

2nd stage

Preparation of
2-methyl-4-amino-5-nitro-N-β-hydroxyethylaniline 1.86 mols (510 g) of β-chloroethyl N-(2-methyl-4-amino-5-nitrophenyl)-carbamate are introduced, at 55° C. in the course of 15 minutes, while stirring, into 2,625 ml of aqueous alcohol solution (30% of $H_2O$, 70% of ethanol) containing 9.32 mols (522 g) of potassium hydroxide. The temperature rises to 72° C. When the addition has ended, one liter of water is added to the reaction mixture and the temperature is kept between 70° and 75° C. The reaction mixture is filtered hot to remove a small amount of insoluble material. 5 liters of ice-water are added to the filtrate and the mixture is neutralised with the aid of acetic acid. The expected product precipitates. It is filtered off with suction, washed with water and recrystallised from alcohol. After drying in vacuo, it has a melting point of 141° C.

| Analysis | Calculated for $C_9H_{13}N_3O_3$ | Found |
|---|---|---|
| C % | 51.18 | 51.13 |
| H % | 6.16 | 6.18 |
| N % | 19.91 | 19.86 |
| O % | 22.75 | 22.64 |

REFERENCE EXAMPLE 2

Preparation of
2-methyl-4-amino-5-nitro-N-methylaniline

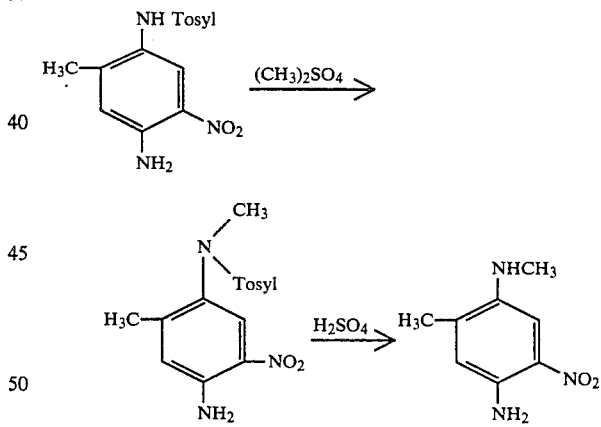

1st stage

Preparation of
3-methyl-4-N-methyl-N-tolylamino-6-nitroaniline 0.05 mol (16.05 g) of 3-methyl-4-N-tosylamino-6-nitroaniline is dissolved in 110 ml of 0.5N sodium hydroxide solution at 40° C. 0.055 mol (6.93 g) of dimethyl sulphate is added dropwise to this solution containing sodium hydroxide, while stirring and maintaining an alkaline pH. After 2 hours at 40° C., the reaction mixture is cooled and the expected product is filtered off with suction. The product is washed with cold 0.5N sodium hydroxide solution and then with water. After two recrystallisations from acetic acid and drying in vacuo, the product has a melting point of 160° C.

2nd stage

Preparation of 2-methyl-4-amino-5-nitro-N-methylaniline 0.239 mol (8 g) of the substituted para-toluenesulphonamide obtained according to the first stage is introduced a little at a time into 40 ml of concentrated sulphuric acid at 0° C., while stirring.

Dissolution is slow. When the solid has dissolved, the reaction mixture is kept at 0° C. for 2 hours and is then poured onto 400 of crushed ice. The expected product precipitates in the form of sulphate. The sulphate is filtered off with suction and dissolved again in water. 2-Methyl-4-amino-5-nitro-N-methylaniline is precipitated by addition of ammonia. The product is filtered off with suction, washed with water and dried in vacuo. After recrystallisation from benzene, it has a melting point of 136° C.

| Analysis | Calculated for $C_8H_{11}N_3O_2$ | Found |
|---|---|---|
| C % | 53.04 | 52.91–53.06 |
| H % | 6.08 | 6.18–6.14 |
| N % | 23.20 | 23.09–23.33 |
| O % | 17.68 | 17.75 |

REFERENCE EXAMPLE 3

Preparation of 2-methyl-4-amino-5-nitro-N-β,γ-dihydroxypropylaniline

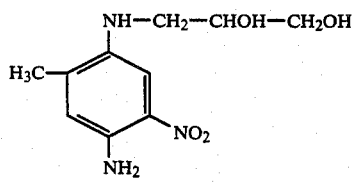

0.2 mol (33.4 g) of 2-methyl-4-amino-5-nitroaniline and 0.1 mol (10 g) of calcium carbonate suspended in 100 ml of water are first heated on a boiling waterbath, while stirring. 0.216 mol (24 g) of 1-chloropropane-2,3-diol is added. The reaction mixture is heated on a boiling waterbath for 24 hours, 0.035 mol (3.5 g) of calcium carbonate and 0.066 mol (7.3 g) of 1-chloropropane-2,3-diol being simultaneously added seven times at intervals of three hours. The reaction mixture is filtered hot and the filtrate is diluted with 60 ml of water. After the filtrate has been cooled at 0° C. for 24 hours, the expected product, which has crystallised, is filtered off with suction. The product is washed with water and recrystallised three times from ethanol. It has a melting point of 150° C.

| Analysis | Calculated for $C_{10}H_{15}N_3O_4$ | Found |
|---|---|---|
| C % | 49.79 | 49.76 |
| H % | 6.22 | 6.21 |
| N % | 17.43 | 17.55 |
| O % | 26.56 | 26.69 |

REFERENCE EXAMPLE 4

Preparation of 2-methyl-4-amino-5-nitro-N-β-aminoethylaniline

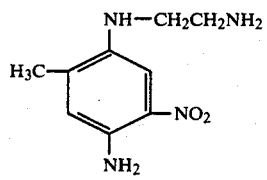

A suspension of 0.05 mol (8.35 g) of 2-methyl-4-amino-5-nitroaniline and 0.035 mol (3.5 g) of calcium carbonate in 100 ml of water are first heated on a boiling waterbath, while stirring. 0.07 mol (14.35 g) of β-bromoethylaniline hydrobromide dissolved in 20 ml of water is added a little at a time, while stirring. After the reaction mixture had been heated on a boiling waterbath for 2 hours, it is filtered hot. After the filtrate has been cooled at 0° C. for 24 hours, the expected product, which has crystallised in the form of the hydrobromide, is filtered off with suction. The crude product is washed with acetone and then recrystallised from boiling water. After filtering off with suction, washing with acetone and drying in vacuo, 2-methyl-4-amino-5-nitro-N-β-aminoethylaniline hydrobromide monohydrate is obtained.

| Analysis | Calculated for $C_9H_{14}N_4O_2 \cdot HBr \cdot H_2O$ | Found |
|---|---|---|
| C % | 34.95 | 35.00 |
| H % | 5.50 | 5.51 |
| N % | 18.12 | 17.98 |
| O % | 15.53 | 15.52 |
| Br % | 25.89 | 25.82 |

The hydrobromide thus obtained is dissolved in water. After the solution has been rendered alkaline with the aid of 2N sodium hydroxide solution, the 2-methyl-4-amino-5-nitro-N-β-aminoethylaniline is filtered off with suction. After washing with water, drying and recrystallisation from ethyl acetate, the product has a melting point of 115° C.

REFERENCE EXAMPLE 5

Preparation of 2-chloro-4-amino-5-nitro-N-β-aminoethylaniline and of the hydrobromide and hydrochloride of this compound

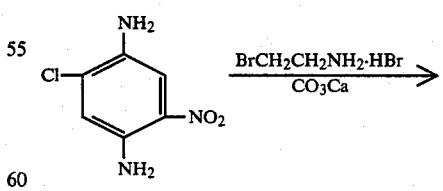

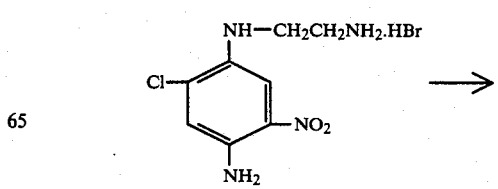

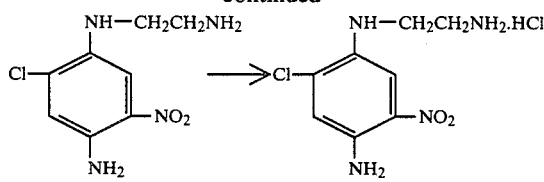

0.1 mol (18.7 g) of 2-chloro-4-amino-5-nitroaniline and 0.1 mol (10 g) of calcium carbonate are introduced into 50 ml of dioxane, and this mixture is brought to the region of 90° C., while stirring. 0.15 mol (30.73 g) of bromoethylamine hydrobromide is added in the course of 30 minutes. When the addition has ended, heating at 90° C. is continued for 4 hours. The reaction mixture is filtered hot. By cooling the filtrate, the expected product crystallises in the form of the monohydrobromide.

The hydrobromide is filtered off with suction, washed with a little cold water and dried. The hydrobromide obtained above is added to 100 ml of water and the mixture is then rendered alkaline, while stirring, to pH 11 with the aid of 10N sodium hydroxide solution. The 2-chloro-4-amino-5-nitro-N-β-aminoethylaniline thus liberated from its hydrobromide is filtered off with suction. After washing with water, drying and recrystallisation from ethyl acetate, the product has a melting point of 133° C.

6.4 g of 2-chloro-4-amino-5-nitro-N-β-aminoethylaniline are dissolved in 100 ml of absolute alcohol. 10 ml of absolute alcohol saturated with hydrogen chloride gas are added. The product precipitates in the form of the hydrochloride. This hydrochloride is filtered off with suction and recrystallised from a 50/50 aqueous alcohol solution. 2-Chloro-4-amino-5-nitro-N-β-aminoethylaniline monohydrochloride which, when dried, has a melting point of about 265° C., with decomposition, is thus obtained.

| Analysis | Calculated for $C_8H_{11}ClN_4O_2 \cdot HCl$ | Found |
|---|---|---|
| C % | 35.97 | 36.00 |
| H % | 4.53 | 4.56 |
| N % | 20.98 | 21.04 |
| O % | 11.98 | 12.09 |
| Cl % | 26.55 | 26.46 |

REFERENCE EXAMPLE 6

Preparation of (3-nitro-4-β-aminoethylamino)-phenoxyethanol

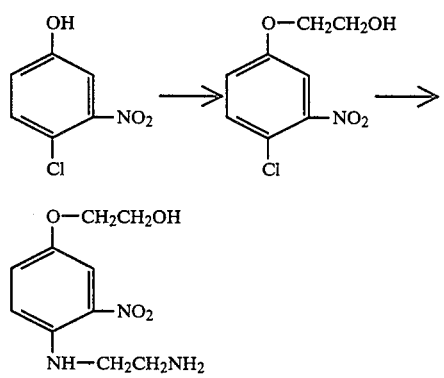

1st stage

Preparation of (3-nitro-4-chloro)-phenoxyethanol 2.5 mols (434 g) of 4-chloro-3-nitrophenol are dissolved in 1,300 ml of dimethylformamide, which has first been heated to 70° C. 3 mols of powdered potassium hydroxide (210 g of 80% pure potassium hydroxide) are added to this solution, and 3 mols (534 g) of glycol bromohydrin are introduced in the course of 30 minutes, while stirring and maintaining the temperature at 70° C. When the addition has ended, the reaction mixture is kept at 70° C. for 1 hour. 1 mol of powdered potassium hydroxide (70 g of 80% pure potassium hydroxide) and 1 mol (178 g) of glycol bromohydrin are then added. After the mixture has been heated for 1 hour, a further 1 mol of potassium hydroxide and 1 mol of glycol bromohydrin are added. Heating is continued for another hour, and the cooled reaction mixture is then poured into 7.5 liters of ice-water. The expected product precipitates. It is filtered off with suction and washed carefully with 3N sodium hydroxide solution and then with water. After drying in vacuo, the product has a melting point of 96° C.

2nd stage

Preparation of (3-nitro-4-β-aminoethylamino)phenoxyethanol 0.4 mol (87 g) of (3-nitro-4-chloro)-phenoxyethanol in 225 ml of ethylenediamine is heated under reflux for 1 hour. The cooled reaction mixture is poured into 500 g of ice-water. The solution is rendered alkaline to pH 10 with the aid of 10N sodium hydroxide solution. The expected product crystallises. It is filtered off with suction, washed with cold water and dried in vacuo at 50° C. It has a melting point of 110° C. After recrystallisation from ethanol, the product has a melting point of 112° C.

| Analysis | Calculated for $C_{10}H_{15}N_3O_4$ | Found |
|---|---|---|
| C % | 49.78 | 49.86 |
| H % | 6.27 | 6.32 |
| N % | 17.42 | 17.35 |
| O % | 26.53 | 26.41 |

REFERENCE EXAMPLE 7

Preparation of 2-N-β-aminoethylamino-5-nitrophenol monohydrochloride monohydrate

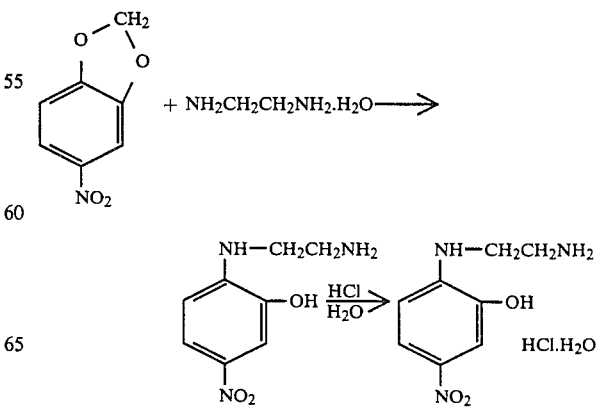

0.179 mol (30 g) of 3,4-methylenedioxynitrobenzene in 150 ml of ethylenediamine is heated on a boiling waterbath for 1 hour, while stirring. After the reaction mixture has been cooled, it is poured into 1,400 ml of icewater, to which 590 ml of hydrochloric acid of d=1.18 have been added. The orange-coloured solution is kept at −10° C. for 2 days. The 2-N-β-aminoethylamino-5-nitrophenol monohydrochloride monohydrate, which has crystallised, is filtered off with suction and washed with the aid of 2N hydrochloric acid solution and then with ice-water. The product is dried in vacuo.

20 g of practically pure product are obtained. Melting point (with decomposition) 253° C.

The product is recrystallised from water and dried.

| Analysis | Calculated for $C_8H_{14}N_3O_4Cl$ | Found |
|---|---|---|
| C % | 38.17 | 38.16 |
| H % | 5.56 | 5.43 |
| N % | 16,70 | 16.94 |
| O % | 25.45 | 25.36 |
| Cl % | 14.11 | 14.27 |

REFERENCE EXAMPLE 8

Preparation of 3-β-aminoethylamino-4-nitrophenol hydrochloride

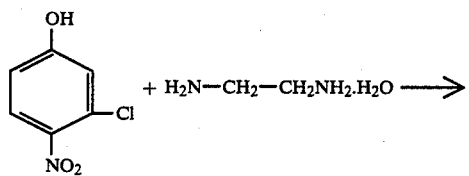

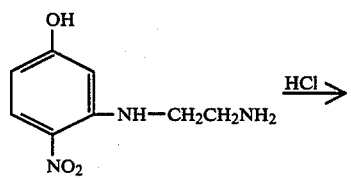

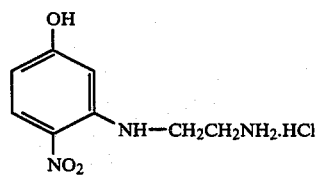

0.432 mol (75 g) of 3-chloro-4-nitrophenol is introduced into 282 ml of ethylenediamine and the reaction mixture is heated on a boiling waterbath for 13 hours. The cooled solution is then poured into 2.6 liters of ice-water to which 1.09 liters of hydrochloric acid (d=1.18) have been added. After the mixture has been cooled to −10° C. for a few hours, 3-β-aminoethylamino-4-nitrophenol hydrochloride crystallises. It is filtered off with suction and washed with an ice-cold 2N hydrochloric acid solution and then with ethanol. After recrystallisation from water, the dried product melts, with decomposition, at a temperature above 260° C.

| Analysis | Calculated for $C_8H_{12}N_3O_3Cl$ | Found |
|---|---|---|
| C % | 41.11 | 41.22 |
| H % | 5.14 | 5.11 |
| N % | 17.99 | 17.92 |
| O % | 20.55 | 20.44 |
| Cl % | 15.20 | 15.38 |

REFERENCE EXAMPLE 9

Preparation of (2-β-aminoethylamino-5-nitro)-phenoxyethanol

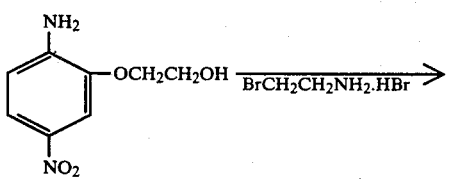

0.39 mol (77.3 g) of (2-amino-5-nitro)-phenoxyethanol in 150 ml of water, to which 23.0 g of calcium carbonate have been added, is first heated to the region of 100° C., while stirring. 0.44 mol (90.15 g) of bromoethylamine hydrobromide in 100 ml of water is added a little at a time, while stirring. Heating in the region of 100° C. is continued for 8 hours, 10 g of calcium carbonate and 30.3 g (0.15 mol) of bromoethylamine hydrobromide in 20 ml of water being added three times at intervals of 2 hours. The reaction mixture is filtered hot. After the filtrate has been cooled, the expected product, in the form of the hydrobromide, is filtered off with suction. The hydrobromide is dissolved in 1,400 ml of water. By addition of 10N sodium hydroxide solution, (2-β-aminoethylamino-5-nitro)-phenoxyethanol is precipitated. The product is filtered off with suction, washed with water and recrystallised from alcohol. It has a melting point of 147° C.

| Analysis | Calculated for $C_{10}H_{15}N_3O_4$ | Found |
|---|---|---|
| C % | 49.75 | 49.92 |
| H % | 6.21 | 6.44 |
| N % | 17.41 | 17.25 |
| O % | 26.53 | 26.90 |

REFERENCE EXAMPLE 10

Preparation of the compound of the formula

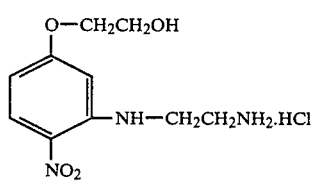

(3-N-β-Aminoethylamino-4-nitro)-phenoxyethanol hydrochloride

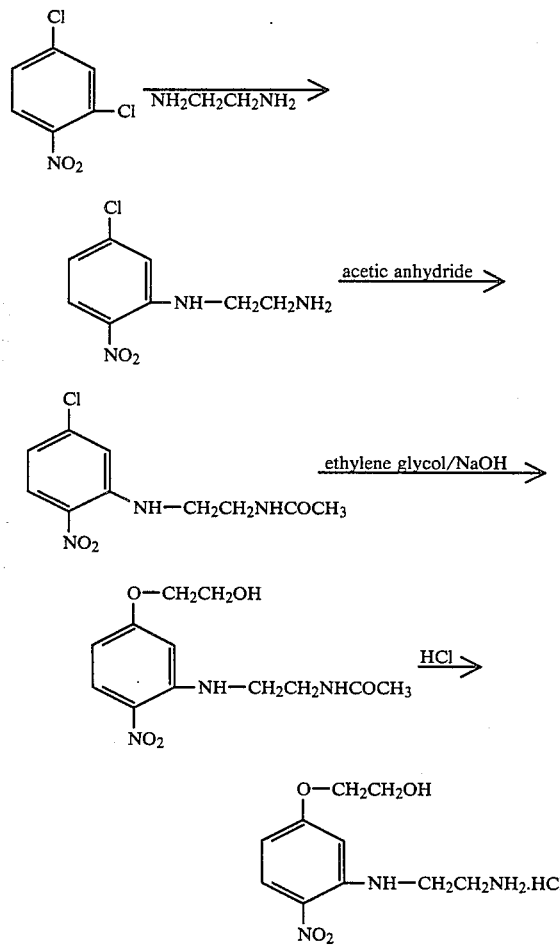

1st stage

Preparation of 2-N-β-acetylaminoethylamino-4-nitrochlorobenzene 1 mol (192 g) of 2,4-dichloronitrobenzene is introduced into 680 ml of ethylenediamine a little at a time, while stirring and maintaining the temperature in the region of 50° C. When the addition has ended, the reaction mixture is kept at 50° C. for 1 hour and is then diluted with 2.5 kg of ice-water. The expected product precipitates. It is filtered off with suction, washed with water and re-suspended in 800 ml of water. 130 ml of acetic anhydride are added, while stirring, and the reaction mixture is then kept at 45° C. for 1 hour. After the mixture has been cooled, the 2-N-β-acetylaminoethylamino-4-nitrochlorobenzene is filtered off with suction, washed with water and dried in vacuo. It has a melting point of 157° C.

2nd stage

Preparation of (3-N-β-acetylaminoethylamino-4-nitro)-phenoxyethanol 0.05 mol (12.87 g) of 2-N-β-acetylaminoethylamino-4-nitrochlorobenzene in 72 g of ethylene glycol, to which 10 ml of 10N sodium hydroxide solution have been added, is heated on a boiling waterbath for 6 hours. After the reaction mixture has been cooled, it is poured into 300 ml of ice-water. The expected product precipitates. The product is filtered off with suction and washed with water. After recrystallisation from water and drying in vacuo, it has a melting point of 118° C.

3rd stage

Preparation of (3-N-β-aminoethylamino-4-nitro)-phenoxyethanol hydrochloride 5 g (0.018 mol) of the acetylated derivative obtained according to the preceding stage are heated to 100° C. in 15 ml of hydrochloric acid of d=1.18 for 5 hours, while stirring.

After the reaction mixture has been cooled, the hydrochloride of the expected product, which has precipitated, is filtered off with suction. After recrystallisation from a mixture of water and alcohol and drying at 80° C. in vacuo, the product has a melting point, with decomposition, of between 256° and 258° C.

| Analysis | Calculated for $C_{10}H_{15}N_3O_4.HCl$ | Found |
|---|---|---|
| C % | 43.25 | 43.24 |
| H % | 5.77 | 5.81 |
| N % | 15.14 | 15.07 |
| O % | 23.06 | 23.14 |
| Cl % | 12.79 | 12.74 |

We claim:

1. A composition suitable for dyeing human hair, which comprises in an acceptable cosmetic medium, an amount effective to dye hair of (a) at least one dyestuff of the formula:

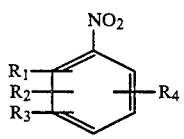

(I)

in which $R_1$ and $R_2$ independently designate hydrogen, amino, alkylamino, —NH—aliphatic—$(X)_m$, dialkylamino or —N—(aliphatic—$(X)_m)_2$, $R_3$ designates hydrogen, OH, alkoxy or —O—aliphatic—$(X)_m$, "aliphatic" designates an aliphatic radical having m+1 free valencies, m designates an integer from 1 to 3 such that if m=1, X represents OH, Cl, $OCH_3$ or $OCH_2CH_2OH$, or, if m designates 2 or 3, X designates OH, and $R_4$ designates hydrogen, alkyl or halogen, with the proviso that at least one of $R_1$, $R_2$ and $R_3$ is other than hydrogen, and that, if $R_1$ and $R_2$ are both other than hydrogen, $R_3$ designates hydrogen, and (b) at least one dyestuff of the formula:

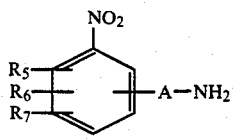

in which $R_5$ designates hydrogen, amino, alkylamino, NH—alkylene—$(X)_m$, N—$(alkyl)_2$, N—(aliphatic$(X)_m)_2$, or $NHCH_2CH_2NH_2$, $R_6$ designates hydrogen, OH, alkoxy, O-aliphatic$(X)_m$ or $O(CH_2)_nNH_2$, $R_7$ designates hydrogen, alkyl or halogen, A designates —Y—$(CH_2)$—$_n$, —$OCH_2$—CHOH—$CH_2$— or

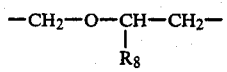

where $R_8$ designates hydrogen or methyl, Y designates oxygen or —NH— and n is an integer from 2 to 4, and m, "aliphatic" and X are as defined above, with the proviso that, if Y designates —NH— and $R_6$ is other than hydrogen, $R_5$ designates hydrogen, and, if Y is an oxygen atom, $R_6$ designates hydrogen, each of alkyl, alkoxy, alkylamino and dialkylamino in formulas (I) and (II) above having 1 to 4 carbon atoms, the shade and chromaticity of the colour obtained with the dyestuff(s) of formula (I) and the shade and chromaticity of the colour obtained with the dyestuff(s) of formula (II) being such that $\Delta H + \Delta C$ is less than or equal to 4.5.

2. A composition according to claim 1 which comprises
(a) at least one dyestuff of formula (I) as defined in claim 1, and
(b) at least one dyestuff of the formula:

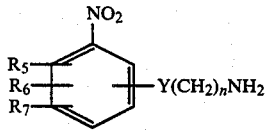

in which $R_5$, $R_6$, $R_7$, Y and n are as defined in claim 1.

3. A composition according to claim 1 which comprises,
(a) at least one dyestuff of formula (I) as defined in claim 1, and
(b) at least one dyestuff of formula (II) as defined in claim 1 in which $R_5$, $R_6$ and $R_7$ are as defined in claim 1 and A designates —$OCH_2CHOH$—$CH_2$— or

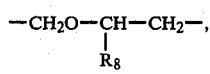

where $R_8$ designates hydrogen or methyl.

4. A composition according to claim 1, in which the dyestuff(s) of formula (II) is/are present in an amount of 1 to 90% by weight, based on the total amount of nitrated dyestuffs.

5. A composition according to claim 4 in which the dyestuff(s) of formula (II) is/are present in an amount from 5 to 70% by weight, based on the total amount of nitrated dyestuffs.

6. A composition according to claim 1, in which the nitrated dyestuffs are present in an amount of 0.005 to 3% by weight, based on the weight of the composition.

7. A composition according to claim 1, which also contains at least one anthraquinone, azo, triarylmethane, benzoquinone or azine dyestuff.

8. A composition according to claim 1, which also contains an oxidation dyestuff in an amount of 0.005 to 10% by weight, based on the total weight of the composition, wherein said oxidation dyestuff is selected from the group consisting of oxidation dyestuff precursors of the para-type, selected from the group consisting of diaminobenzenes, diaminopyridines and aminophenols, wherein the functional groups are in the para-position relative to one another, oxidation dyestuff precursors of the ortho type, wherein the functional groups are in the ortho-position relative to one another, and, compounds selected from the group consisting of meta-diaminobenzenes, meta-diaminopyridines, meta-aminophenols, meta-diphenols and also phenols, pyrazolones, mono- or di-hydroxylated derivatives of naphthalene and diketone derivatives.

9. A composition according to claim 1, which has a pH of 1 to 11.5.

10. A composition according to claim 9 which has a pH of 4 to 10.5.

11. Process for dyeing human hair, which comprises applying thereto at least one composition as defined in claim 1, fixing the composition for 2 minutes to 1 hour 30 minutes and rinsing said hair, optionally washing said hair, and drying said hair.

12. Process for dyeing human hair, which comprises applying thereto a composition containing either at least one dyestuff of formula (I) or at least one dyestuff of formula (II), as defined in claim 1, in a first step, and after fixing, applying either at least one dyestuff of formula (II) or at least one dyestuff of formula (I), respectively, these dyestuffs being chosen such that $\Delta H + \Delta \leq 4.5$.

13. A composition suitable for dyeing human hair which comprises in an acceptable cosmetic medium, an amount effective to dye hair of
(a) at least one dyestuff of the formula:

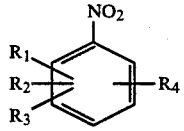

in which $R_1$ and $R_2$ independently designate hydrogen, amino alkylamino, —NH—aliphatic—$(X)_m$, dialkylamino or —N—(aliphatic—$(X)_m)_2$, $R_3$ designates hydrogen, OH, alkoxy or —O—aliphatic—$(X)_m$, "aliphatic" designates a branched or straight chain radical with 1 to 4 carbon atoms where m designates an integer from 1 to 3 such that if m=1, X represents OH, Cl, $OCH_3$ or $OCH_2CH_2OH$, or, if m designates 2 or 3, X designates OH, and $R_4$ designates hydrogen, alkyl or halogen, with the proviso that at least one of $R_1$, $R_2$ and $R_3$ is other than hydrogen, and that, if $R_1$ and $R_2$ are both other than hydrogen, $R_3$ designates hydrogen, and
(b) at least one dyestuff of the formula:

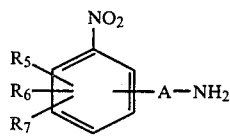 (II)

in which $R_5$ designated hydrogen, amino, alkylamino, NH—alkylene—$(X)_m$, N—(alkyl)$_2$, N—(aliphatic$(X)_m)_2$, or NHCH$_2$CH$_2$NH$_2$, $R_6$ designates hydrogen, OH, alkoxy, O—aliphatic$(X)_m$ or O(CH$_2$)$_n$NH$_2$, $R_7$ designates hydrogen, alkyl or halogen, A designates —Y—(CH$_2$)—$_n$, —OCH$_2$—CHOH—CH$_2$— or

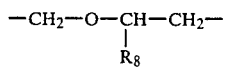

where $R_8$ designates hydrogen or methyl, Y designates oxygen or —NH— and n is an integer from 2 to 4, and m, "aliphatic" and X are as defined above, with the proviso that, if Y designates —NH— and $R_6$ is other than hydrogen, $R_5$ designates hydrogen, and, if Y is an oxygen atom, $R_6$ designates hydrogen, each of alkyl, alkoxy, alkylamino and dialkylamino in formulas (I) and (II) above having 1 to 4 carbon atoms, the shade and chromaticity of the colour obtained with the dyestuff(s) of formula (I) and the shade and chromaticity of the colour obtained with the dyestuff(s) of formula (II) being such that $\Delta H + \Delta C$ is less than or equal to 4.5.

* * * * *